United States Patent
Abraham-Fuchs et al.

(10) Patent No.: US 7,186,216 B2
(45) Date of Patent: Mar. 6, 2007

(54) QUALITY CONTROL SYSTEM IN DISEASE MANAGEMENT SERVICES FOR CHECKING ADHERENCE TO THERAPY

(75) Inventors: Klaus Abraham-Fuchs, Erlangen (DE); Johannes Bieger, München (DE); Eva Rumpel, Erlangen (DE); Kai-Uwe Schmidt, Erlangen (DE); Daniel Tietze, Spardorf (DE)

(73) Assignee: Siemens Aktiengesellschaft, München ( * ) Notice: Subject to any disclaimer, the term of this patent is extended or adjusted under 35 U.S.C. 154(b) by 42 days.

(21) Appl. No.: 10/212,690

(22) Filed: Aug. 7, 2002

(65) Prior Publication Data
US 2003/0040661 A1 Feb. 27, 2003

(30) Foreign Application Priority Data
Aug. 7, 2001 (DE) ................. 101 38 708

(51) Int. Cl.
*A61B 5/00* (2006.01)
(52) U.S. Cl. ............... 600/300; 434/262; 128/920
(58) Field of Classification Search ........ 434/236–238, 434/262, 322, 323, 350, 362, 235; 600/300–301, 600/587, 595; 342/573.1; 128/904, 920, 128/897; 705/2–4; 273/429–432
See application file for complete search history.

(56) References Cited

U.S. PATENT DOCUMENTS

| | | | |
|---|---|---|---|
| 5,601,435 A | 2/1997 | Quy | |
| 5,799,282 A * | 8/1998 | Rakshit et al. | 434/350 |
| 5,913,310 A * | 6/1999 | Brown | 600/300 |
| 6,024,699 A * | 2/2000 | Surwit et al. | 600/300 |
| 6,171,112 B1 * | 1/2001 | Clark et al. | 434/322 |
| 6,280,198 B1 * | 8/2001 | Calhoun et al. | 434/236 |
| 6,334,778 B1 * | 1/2002 | Brown | 434/258 |
| 6,454,705 B1 * | 9/2002 | Cosentino et al. | 600/300 |
| 6,494,830 B1 * | 12/2002 | Wessel | 600/300 |
| 6,514,079 B1 * | 2/2003 | McMenimen et al. | 434/219 |
| 6,767,211 B2 * | 7/2004 | Hall et al. | 434/236 |
| 2003/0219709 A1 * | 11/2003 | Olenick et al. | 434/350 |

FOREIGN PATENT DOCUMENTS

| | | |
|---|---|---|
| EP | 0 922 434 A1 | 6/1999 |
| EP | 1 110 500 A2 | 6/2001 |
| WO | WO 99/04043 | 1/1999 |
| WO | WO 00/62177 | 10/2000 |
| WO | WO 01/44953 A1 | 6/2001 |
| WO | WO 01/45014 A1 | 6/2001 |

OTHER PUBLICATIONS

European Search Report.

* cited by examiner

*Primary Examiner*—Max F. Hindenburg
*Assistant Examiner*—Michael C Astorino
(74) *Attorney, Agent, or Firm*—Alexander J. Burke

(57) ABSTRACT

Quality control system in Disease Management Services involving education, development and motivation of patients suffering from widespread chronic diseases, such as diabetes, asthma or hypertension, possibly involving telemonitoring of critical body values and resultant early identification and avoidance of risk situations, where an automatic delivery monitoring facility is provided which monitors the receipt of all messages and information by the patients and, if appropriate, informs a control station in order to eliminate access problems.

19 Claims, 2 Drawing Sheets

QUALITY CONTROL SYSTEM IN DISEASE MANAGEMENT SERVICES FOR CHECKING ADHERENCE TO THERAPY

FIELD OF THE INVENTION

The invention relates to a quality control system in Disease Management Services involving education, development and motivation of patients suffering from widespread chronic diseases, such as diabetes, asthma or hypertension, possibly involving telemonitoring of critical body values and resultant early identification and avoidance of risk situations.

BACKGROUND OF THE INVENTION

Disease Management Service Providers (DMSPs) are a growth sector on a worldwide scale as medical service providers. Their business concept is based primarily on education, development and motivation of patients combined with telemonitoring of critical body values and, consequently, early identification and avoidance of risk situations. Disease Management Services typically look after patients who are suffering from a widespread chronic disease, such as diabetes, asthma or hypertension, which means that large numbers of patients are looked after using a largely standardized treatment plan over long periods of time (typically months or years). This results in significant increased cost efficiency as compared with traditional patient care. In this case, this cost efficiency is achieved, inter alia, by the greatest possible degree of automation of the patient care, for example as a result of patient training material automatically being sent at stipulated intervals, advisory calls being made, or measured values, such as the patient's blood pressure, being sent in digital form to a control center where they are automatically assessed and, in the event of limit values being exceeded or not reached, a fax or an e-mail containing an appropriate recommended treatment is sent to the physician providing the care.

Generally, the costs for this form of patient care are borne by the health insurance companies. These are increasingly demanding evidence of the long-term cost efficiency of such intervention from the DMSPs. Since the pathologies for which care is provided are essentially those where the patients need to change habitual but unhealthy behavior (for example stopping smoking, changing diet etc.), the desired success can be achieved only by providing the patient with an insight into and an understanding of his situation. For this reason, patient education, that is to say working through the appropriate training material and comprehension of its content, is of particular importance.

Hence, in order to be able to answer the very important question of whether the patient to be treated has a) received his assigned training material and b) has studied it and also understood it as specified, the service provider has no other option to date than to subject the patient to a telephone assessment which, depending on the kind of patient, can be very complex and laborious.

On the other hand, the DMSP cannot dispense with this practice, since firstly it is a form of care documentation for health insurance companies, and secondly health insurance companies increasingly wish to pay out on the basis of success, and hence the service providers have particularly great motivation for the patient to internalize and implement the training material.

SUMMARY OF THE INVENTION

The invention is therefore based on the object of developing a quality control system of the type mentioned in the introduction such that the patient's level of knowledge within the context of the individual training program can be automatically checked.

BRIEF DESCRIPTION OF THE DRAWINGS

More in-depth details and special features of the inventive quality control system can be found in the appended drawings, in which.

DESCRIPTION OF THE PREFERRED EMBODIMENTS

The invention achieves this object by first providing an automatic delivery monitoring facility which monitors the receipt of all messages and information by the patients and, if appropriate, informs a control station in order to eliminate access problems. If the documents are sent by e-mail, this can be done by virtue of an appropriate e-mail response, and the online version allows this to be done by recording the activity of the respective patient (for example using log files).

Figure 1:
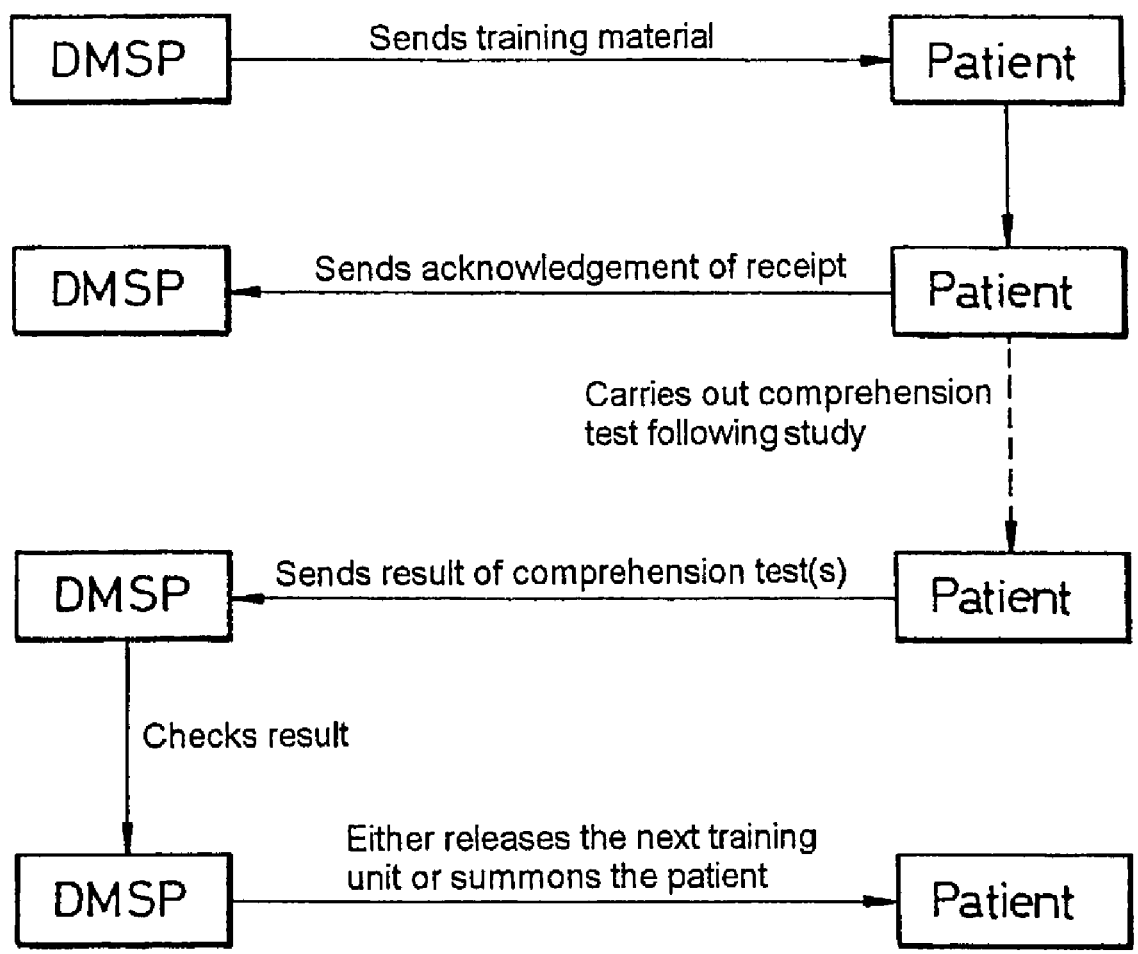
FIG. 1 shows a schematic flowchart for the relationships between the Disease Management Service Provider (DMSP) and the patient.
Figure 2:
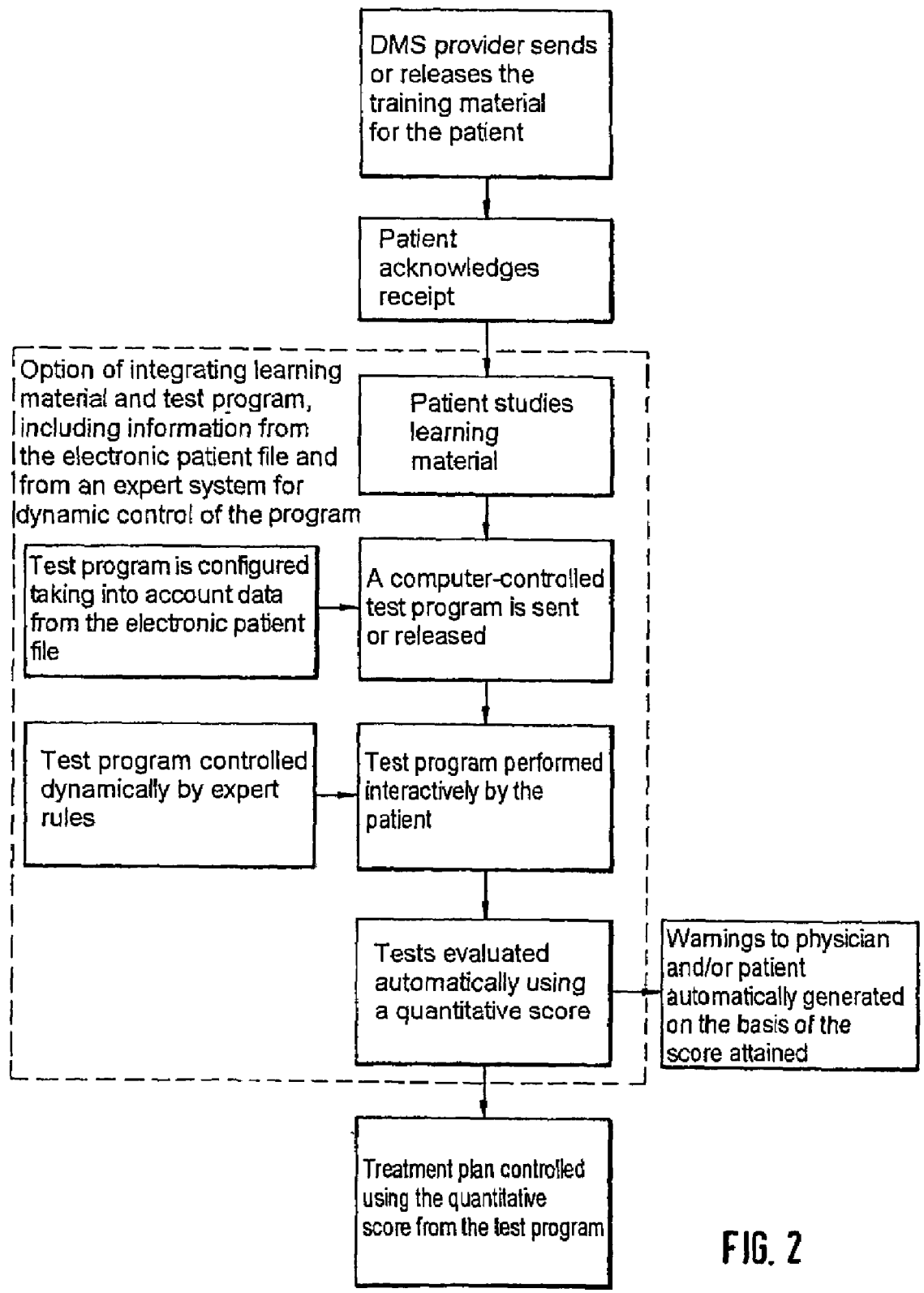
FIG. 2 shows a detailed chart of a course of treatment using the inventive quality control system.

With reference to FIGS. 1 and 2, the quality control system of the present invention provides that the DMSP sends training material to a patient, who acknowledges receipt of the training material. The patient studies the training material and receives a computer-controlled test program. The test program may be controlled dynamically by expert rules. The patient performs the test program interactively and sends the test results to the DMSP that checks the results. The DMSP releases the next training program to the patient or summons the patient for further consolation, depending on the quantitative test score. The DMSP controls the treatment plan using the quantitative score from the test program.

By way of further explanation, the patient is subjected to a comprehension test whose receipt by the patient is automatically monitored in the Disease Management Service Provider's sending center and whose performance results are preferably evaluated fully automatically, with a further feature of the invention involving the evaluation unit being able to generate automatic warnings to the physician, to the patient or to the respective health insurance company.

These comprehension tests make it possible to establish whether the patient has understood the lessons and advice and information sufficiently, it also being possible for these comprehension tests to be used for the purpose of refreshing lessons from the past. If the patient is overtaxed or is permanently uninterested, he can then be summoned and the appropriate measures can be discussed with him. If appropriate, the only sensible consequence of permanent failure of coordinated cooperation may be to terminate the treatment and to contact the health insurance company.

The tests can, by way of example, be questionnaires (multiple choice or full answers) or else interactive "computer games" in which typical scenarios are enacted, with the patient having to take action at a suitable point.

The inventive quality control system can be developed such that the tests with a positive assessment cause automatic release for further tests and/or additional training units.

In this case, it has been found to be particularly expedient if the tests have no rigid structure, but rather are designed to be flexible using software expert rules in the background, so that the test questions can be matched to the patient on an individual basis, for example depending on age, level of education, other illnesses, disease history, etc., the information required for this purpose being able to be taken from an "electronic patient file" of the DMS provider by the expert-system.

In one development of the invention, the course of the test questions can also be altered dynamically, for example such that whenever an incorrect response is given the question is posed in a different way, in order to identify and eliminate possible misunderstandings by the patient.

Ultimately, learning material in an intelligent form combines a lesson with testing of the success of learning while including the functionality of the test variations above.

The test results can also be used to obtain the following additional benefit: a dynamically structured treatment plan for the patient contains treatment instructions for the treating physician and for the patient, together with times of the intended performance, and logic rules which result in the treatment instructions being performed. This can take the form, by way of example, that treatment regime A needs to be observed while the patient's weight is below 80 kg, but that treatment based on regime B needs to be carried out if his weight is above 80 kg. The results of the learning success tests can be used, in the form of quantified marks or scores, for automatically controlling such a treatment plan.

The invention claimed is:

1. An automated quality control system for a disease management service (DMS) whose patients suffer from diseases requiring long-term attention by the patient, the system comprising:
   a delivery unit that sends training material to a patient suffering from a disease requiring long-term attention by the patient, the training material including educational material relating to and aiding patient self-treatment and related to the disease and a comprehension test that is to be taken by the patient after having received the educational material and that determines whether the patient has understood the educational material;
   a receipt acknowledgment unit that automatically confirms receipt of the training material by the patient;
   a test evaluation unit that automatically evaluates answers to the comprehension test that has been taken by the patient and returned to the DMS; and
   a telemonitoring system that monitors body parameter values of the patient.

2. The quality control system of claim 1, wherein said test evaluation unit automatically generates a warning based on a negative automatic evaluation of the answers to the comprehension test by said test evaluation unit, the warning being sent from the DMS to at least one of the patient, a care giver for the patient, and a health insurer for the patient.

3. The quality control system of claim 2, wherein said delivery unit sends further training material to the patient based on a positive automatic evaluation of the answers to the comprehension test by said test evaluation unit.

4. The quality control system of claim 1, wherein said delivery unit sends further training material to the patient based on a positive automatic evaluation of the answers to the comprehension test by said test evaluation unit.

5. The quality control system of claim 1, further comprising an expert system operating in accordance with predetermined rules, said expert system generating rules for generation of questions for the comprehension test based on the disease suffered by the patient and on a background of the patient, so that the questions in the comprehension test vary from patient to patient.

6. The quality control system of claim 1, wherein said test evaluation unit operates dynamically and adds or amends a later question in the comprehension test if the patient provides an incorrect response to a question in the comprehension test.

7. The quality control system of claim 1, wherein said test evaluation unit provides a quantified score from the evaluation of the answers to the comprehension test, and wherein the quantified score is used by the quality control system to produce a dynamically structured treatment plan for the patient.

8. The quality control system of claim 7, wherein said test evaluation unit generates a warning based on the quantified score, the warning being sent from the DMS to at least one of the patient, a care giver for the patient, and a health insurer for the patient.

9. The quality control system of claim 8, wherein said delivery unit sends further said training material to the patient based on the quantified score.

10. An automated quality control method for a disease management service (DMS) whose patients suffer from diseases requiring long-term attention by the patient, the method comprising the steps of:
    sending training material to a patient suffering from a disease requiring long-term attention by the patient, the training material including educational material relating to and aiding patient self-treatment and related to the disease and a comprehension test that is to be taken by the patient after having received the educational material and that determines whether the patient has understood the educational material;
    automatically acknowledging that the training material has been received by the patient;
    automatically evaluating answers to the comprehension test that has been taken by the patient and returned to the DMS; and
    monitoring body parameter values of the patient.

11. The quality control method of claim 10, further comprising the step of automatically generating warnings based on a negative automatic evaluation of the answers to the comprehension test, the warnings being sent from the DMS to at least one of the patient, a care giver for the patient, and a health insurer for the patient.

12. The quality control method of claim 11, further comprising the step of sending further training material to the patient based on a positive automatic evaluation of the answers to the comprehension test.

13. The quality control method of claim 10, further comprising the step of generating rules for generation of questions for the comprehension test based on the disease suffered by the patient and on a background of the patient, so that the questions in the comprehension test vary from patient to patient.

14. The quality control method of claim 10, further comprising the step of revising a later question in the comprehension test when the patient provides an incorrect response to a question in the comprehension test.

15. The quality control method of claim 10, further comprising the step of providing a quantified score from the evaluation of the answers to the comprehension test, and wherein the quantified score is used to produce a dynamically structured treatment plan for the patient.

16. The quality control method of claim 15, further comprising the step of generating a warning based on the quantified score, the warning being sent from the DMS to at least one of the patient, a care giver for the patient, and a health insurer for the patient.

17. The quality control method of claim 16, further comprising the step of sending further training material to the patient based on the quantified score.

18. The quality control method of claim 10, wherein said step of sending training material further includes sending motivational material for motivating said patient to continue self-treatment.

19. The quality control system of claim 1, wherein said training material further includes motivational material for motivating said patient to continue self-treatment.

* * * * *